(12) United States Patent
Nichols et al.

(10) Patent No.: US 6,413,977 B1
(45) Date of Patent: Jul. 2, 2002

(54) CHROMENO[4,3,2-DE]ISOQUINOLINES AS POTENT DOPAMINE RECEPTOR LIGANDS

(75) Inventors: David E. Nichols, West Lafayette; Russell A. Grubbs, Lafayette, both of IN (US); Richard B. Mailman, Chapel Hill, NC (US)

(73) Assignees: Purdue Research Foundation, West Lafayette, IN (US); The University of North Carolina at Chapel Hill, Chapel Hill, NC (US)

(*) Notice: Subject to any disclaimer, the term of this patent is extended or adjusted under 35 U.S.C. 154(b) by 0 days.

(21) Appl. No.: 09/598,127

(22) Filed: Jun. 21, 2000

Related U.S. Application Data (60) Provisional application No. 60/140,166, filed on Jun. 21, 1999.

(51) Int. Cl.$^7$ .................. A61K 31/44; C07D 471/00
(52) U.S. Cl. ............................ 514/285; 546/62
(58) Field of Search .................. 546/62; 514/285

(56) References Cited

FOREIGN PATENT DOCUMENTS

| DE | 25 29 580 A1 | 2/1976 |
| GB | 2105 323 A | 6/1982 |
| WO | 9911649 | * 3/1999 |

* cited by examiner

*Primary Examiner*—Alan L. Rotman
*Assistant Examiner*—Binta Robinson
(74) *Attorney, Agent, or Firm*—Barnes & Thornburg

(57) ABSTRACT

Novel dopamine receptor ligands of the formula:

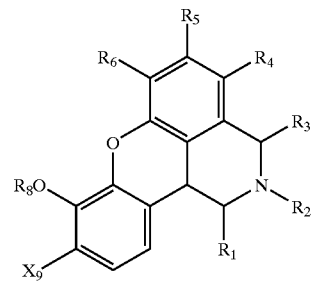

pharmaceutical formulations of such compounds, and a method using such compounds for treating a patient suffering from dopamine-related dysfunction of the central or peripheral nervous system, are described. The compounds are expected to be useful in treating Parkinson's disease, improving cognition, improving memory, improving the negative symptoms of schizophrenia, improving attention-deficit hyperactivity disorder and related developmental disorders, treating substance abuse disorders, and in treating various peripheral conditions where changes in dopamine receptor occupation affects physiological function, including organ perfusion, cardiovascular function, and selected endocrine and immune system functions.

26 Claims, 4 Drawing Sheets

Binding of dinoxyline to striatal $D_1$ receptors.

Figure 1: Binding of dinoxyline to striatal $D_1$ receptors.

Figure 2: Binding of dinoxyline to primate $D_1$ receptors in C-6 cells.

Figure 3: Binding of dinoxyline to rat striatal $D_2$ receptors.

Figure 4: Effect of Dinoxyline in the Rat Unilateral 6-OHDA-lesion Model.

CHROMENO[4,3,2-DE]ISOQUINOLINES AS POTENT DOPAMINE RECEPTOR LIGANDS

CROSS REFERENCE TO RELAYED APPLICATIONS

This application claims priority under 35 U.S.C. § 119 U.S. Provisional Application No. 60/140,166, filed Jun. 21, 1999 is expressly incorporated by reference herein.

GOVERNMENT RIGHTS CLAUSE

This invention was made with Government support under Grant No. MH42705 awarded by the National Institute of Health. The Government has certain rights in the invention.

FIELD OF THE INVENTION

This invention is directed to novel ligands for dopamine receptors. More particularly, the present invention is directed to optionally substituted 1,2,3,11b-tetrahydrochromeno[4,3,2-de]isoquinoline compounds and their use in pharmaceutical formulations for treatment of dopamine-related dysfunction of the central and peripheral nervous system.

BACKGROUND AND SUMMARY OF THE INVENTION

Dopamine, a neurotransmitter in the central nervous system, has been implicated in numerous neurological disorders. For example, it has been hypothesized that excess stimulation of dopamine receptor subtypes may be linked to schizophrenia. Additionally, it is generally recognized that either excessive or insufficient functional dopaminergic activity in the central and/or peripheral nervous system may cause hypertension, narcolepsy, and other behavioral, neurological, physiological, and movement disorders including Parkinson's disease, a chronic, progressive disease characterized by an inability to control the voluntary motor system.

Dopamine receptors have traditionally been classified into two families (the $D_1$ and $D_2$ dopamine receptor families) based on pharmacological and functional evidence. $D_1$ receptors preferentially recognize the phenyltetrahydrobenzazepines and generally lead to stimulation of the enzyme adenylate cyclase, whereas $D_2$ receptors recognize the butyrophenones and benzamides and often are coupled negatively (or not at all) to adenylate cyclase. It is now known that at least five genes exist that code for subtypes of dopamine receptors: the $D_1$, $D_2$, $D_3$, $D_4$ and $D_5$ receptor subtypes. The traditional classification, however, remains useful, with the $D_1$-like class comprising the $D_1$ ($D_{1A}$) and the $D_5$ ($D_{1B}$) receptor subtypes, whereas the $D_2$-like class consists of the $D_2$, $D_3$ and $D_4$ receptor subtypes. Variation can occur also through splice variants (e.g., the $D_{2L}$ and $D_{2S}$ splice variants), as well as through different alleles (e.g., multiple repeats of the $D_4$ gene).

Central nervous system drugs exhibiting affinity for the dopamine receptors are generally classified not only by their receptor selectivity, but further by their agonist (receptor activating) or antagonist (receptor blocking) activity. While the physiological activities associated with the interaction of dopamine with the various receptor subtypes are not fully understood, it is known that ligands exhibiting selectivity for a particular receptor subtype will produce more or less predicable neuropharmacological results. The availability of selective dopamine receptor antagonist and agonist compounds permits the design of experiments to enhance understanding of the many functional roles of $D_1$ receptors and can lead to new treatments for various central and peripheral nervous system disorders. In addition, if agonists were available with high affinity for both the $D_1$ and $D_2$ receptors, these agonists could be used under circumstances where binding to both $D_1$ and $D_2$ receptors is beneficial.

The early focus of dopamine receptor studies was on the $D_2$ family, but a critical role of the dopamine $D_1$ receptor in nervous system function has become apparent recently. That early work on selective $D_1$ receptor ligands primarily focused on molecules from a single chemical class, the phenyltetrahydrobenzazepines, such as the antagonist SCH23390 (1):

SCH23390

SKF 38393

Several of the phenyltetrahydrobenzazepines were found to be $D_1$ receptor agonists; however, the agonists derived from this class [including, for example, SKF38393 (+)-2] generally were partial agonists. Even SKF82958, purported to be a full agonist, recently has been shown not to have full intrinsic efficacy in preparations with decreased receptor reserve. The differentiation between $D_1$ agonists of full and partial efficacy is important to the medical research community because this may influence the actions of these compounds on complex central nervous system mediated events. For example, two full agonists (dihydrexidine and A-77636) have exceptional antiparkinsonian effects in the MPTP-treated monkey model, whereas partial agonists are without significant activity. More recent data suggest that full and partial agonists also differ in their effects on other complex neural functions. In addition, there are receptor-mediated events (e.g., recruitment of G proteins and associated receptor kinases) that can affect agonist activity. These latter biochemical events may occur independently of the changes in second messenger levels (e.g., cAMP) mediated by a drug.

Accordingly, researchers have directed their efforts to design ligands that are full agonists (i.e., have full intrinsic efficacy) for the $D_1$ receptor. One such compound is dihydrexidine (3), a hexahydrobenzo[α]phenanthridine of the formula:

Dihydrexidine

The structure of dihydrexidine (3) is unique from other $D_1$ agonists because the accessory ring system is tethered, making the molecule relatively rigid. Molecular modeling studies of dihydrexidine (3) have shown that the compound has a limited number of low energy conformations, and the aromatic rings are held in a relatively coplanar arrangement in all of these conformations. The recent elucidation of the configuration of the active enantiomer of dihydrexidine (3) was consistent with predictions from this model.

Unlike other high affinity, high intrinsic activity $D_1$ agonists like 3-substituted aminomethylisochromans, dihydrexidine (3) provided a semi-rigid template for developing a dopamine ligand model. The essential features of this model include the presence of a transoid β-phenyldopamine moiety, an equatorially oriented electron lone pair on the basic nitrogen atom, and near coplanarity of the pendant phenyl ring with the catechol ring. The dihydrexidine-based model has a transoid β-phenyldopamine moiety, whereas the dopaminergic phenyltetrahydrobenzazepines have a cisoid β-phenyldopamine conformation. The dihydrexidine-based model has served as the basis for the design of additional $D_1$ receptor agonists. The design and synthesis of $D_1$ receptor agonists having high intrinsic activity is important to the medical research community due to the potential use of full agonists to treat complex central nervous system mediated events, and also conditions in which peripheral dopamine receptors are involved. For example, the compositions of the present invention have potential use as agents for lowering blood pressure, and for affecting lung and kidney function.

One embodiment of the present invention is a novel class of dopamine receptor agonists of the general formula:

and pharmaceutically acceptable salts thereof, and pharmaceutical formulations of such compounds. The present compounds are useful for treating patients having a dopamine-related dysfunction of the central nervous system (as evidenced by an apparent neurological, psychological, physiological, or behavioral disorder), as well as conditions in which peripheral dopamine receptors are involved (including target tissues such as the kidney, lung, endocrine, and cardiovascular systems).

DETAILED DESCRIPTION OF THE INVENTION

There is provided in accordance with the present invention a compound of the general formula:

and pharmaceutically acceptable salts thereof wherein $R_1$–$R_3$ are hydrogen, $C_1$–$C_4$ alkyl or $C_2$–$C_4$ alkenyl; $R_8$ is hydrogen, $C_1$–$C_4$ alkyl or a phenoxy protecting group; $X_9$ is hydrogen, halo including chloro, fluoro and bromo, or a group of the formula —OR wherein R is hydrogen, $C_1$–$C_4$ alkyl or a phenoxy protecting group, and $R_4$, $R_5$ and $R_6$ are independently selected from the group consisting of hydrogen, $C_1$–$C_4$ alkyl, phenyl, halo, or a group —OR wherein R is as defined above, and when $X_9$ is a group of the formula —OR, the groups $R_8$ and R can be taken together to form a group of the formula —$CH_2$—.

The term "$C_2$–$C_4$ alkenyl" refers to allyl, 2-butenyl, 3-butenyl, and vinyl.

The term "$C_1$–$C_4$ alkyl" as used herein refers to branched or straight chain alkyl groups comprising one to four carbon atoms, including, but not limited to, methyl, ethyl, propyl, isopropyl, n-butyl, t-butyl and cyclopropylmethyl.

In one embodiment at least one of $R_4$, $R_5$ or $R_6$ is hydrogen. In another embodiment at least two of $R_4$, $R_5$ or $R_6$ is hydrogen.

The term "pharmaceutically acceptable salts" refers to those salts formed using organic or inorganic acids which salts are suitable for use in humans and lower animals without undesirable toxicity, irritation, allergic response and the like. Acids suitable for forming pharmaceutically acceptable salts of biologically active compounds having amine functionability are well known in the art. The salts can be prepared according to conventional methods in situ during the final isolation and purification of the present compounds, or separately by reacting the isolated compounds in free base form with a suitable salt forming acid.

The term "phenoxy protecting group" as used herein refers to substituents on the phenolic oxygen which prevent undesired reactions and degradations during synthesis and which can be removed later without effect on other functional groups on the molecule. Such protecting groups and the methods for their application and removal are well known in the art. They include ethers, such as cyclopropylmethyl, cyclohexyl, allyl ethers and the like; alkoxyalkyl ethers such as methoxymethyl or methoxyethoxymethyl ethers and the like; alkylthioalkyl ethers such as methylthiomethyl ethers; tetrahydropyranyl ethers; arylalkyl ethers such as benzyl, o-nitrobenzyl, p-methoxybenzyl, 9-anthrylmethyl, 4-picolyl ethers and the like; trialkylsilyl ethers such as trimethylsilyl, triethylsilyl, t-butyldimethylsilyl, t-butyldiphenylsilyl ethers and the like; alkyl and aryl esters such as acetates, propionates, butyrates, isobutyrates, trimethylacetates, benzoates and the like; carbonates such as methyl, ethyl, 2,2,2-trichloroethyl, 2-trimethylsilylethyl, benzyl and the like; and carbamates such as methyl, isobutyl, phenyl, benzyl, dimethyl and the like.

The term "$C_1$–$C_4$ alkoxy" as used herein refers to branched or straight chain alkyl groups comprising one to four carbon atoms bonded through an oxygen atom, including but not limited to, methoxy, ethoxy, propoxy and t-butoxy.

Further, in accordance with other embodiments of this invention the present compounds can be formulated in conventional drug dosage forms for use in methods for treating a patient suffering from dopamine-related dysfunction of the central or peripheral nervous system. Effective doses of the present compounds depend on many factors, including the indication being treated, the route of administration, and the overall condition of the patient. For oral administration, for example, effective doses of the present compounds are expected to range from about 0.1 to about 50 mg/kg, more typically about 0.5 to about 25 mg/kg. Effective parenteral doses can range from about 0.01 to about 5 mg/kg of body weight. In general, treatment regimens utilizing compounds in accordance with the present invention comprise administration of from about 1 mg to about 500 mg of the compounds of this invention per day in multiple doses or in a single dose.

Liquid dosage forms for oral administration may include pharmaceutically acceptable emulsions, microemulsions, solutions, suspensions, and syrups containing inert diluents commonly used in the art, such as water. Such compositions may also comprise adjuvants such as wetting agents, emulsifying and suspending agents, sweetening, and flavoring agents. Injectable preparations of the compounds of the present invention can be formulated utilizing art-recognized products by dispersing or dissolving an effective dose of the compound in a parenterally acceptable diluent such as water, or more preferably isotonic sodium chloride solution. The parenteral formulations can be sterilized using art-recognized microfiltration techniques.

The compounds of this invention can also be formulated as solid dosage forms for oral administration such as capsules, tablets, powders, pills and the like. Typically the active compound is admixed with an inert diluent or carrier such as sugar or starch and other excipients appropriate for the dosage form. Thus, tableting formulations will include acceptable lubricants, binders and/or disintegrants. Optionally powder compositions comprising an active compound of this invention and, for example, a starch or sugar carrier can be filled into gelatin capsules for oral administration. Other dosage forms of the compounds of the present invention can be formulated using art-recognized techniques in forms adapted for the specific mode of administration.

One compound provided in accordance with the present invention is (±)-8,9-dihydroxy- 1,2,3,11b-tetrahydrochromeno[4,3,2-de]isoquinoline hydrobromide denominated hereinafter as "dinoxyline." Dinoxyline is synthesized from 2,3-dimethoxyphenol, as depicted in Scheme 1. The phenolic group is protected as the methoxymethyl ("MOM") derivative followed by treatment with butyllithium, then with the substituted borolane illustrated, to afford the borolane derivative 2.

As shown in Scheme 1, this borolane derivative is then employed in a Pd-catalyzed Suzuki type cross coupling reaction with 5-nitro-4-bromoisoquinoline. The resulting coupling product 4 is then treated with toluenesulfonic acid in methanol to remove the MOM protecting group of the phenol. Simple treatment of this nitrophenol 5 with potassium carbonate in DMF at 80° C. leads to ring closure with loss of the nitro group, affording the basic tetracyclic chromenoisoquinoline nucleus 6. Simple catalytic hydrogenation causes reduction of the nitrogen-containing ring to yield 7. Use of boron tribromide to cleave the methyl ether linkages gives the parent compound 8.

It is apparent that by appropriate substitution on the isoquinoline ring a wide variety of substituted compounds can be obtained. Substitution onto the nitrogen atom in either 6 or 7, followed by reduction will readily afford a series of compounds substituted with lower alkyl groups on the nitrogen atom. Likewise, the use of alkyl substituents on the 1, 3, 6, 7, or 8 positions of the nitroisoquinoline 3 would lead to a variety of ring-substituted compounds. In addition, the 3-position of 6 can also be directly substituted with a variety of alkyl groups. Similarly, replacement of the 4-methoxy group of 2, in Scheme 1, with fluoro, chloro, or alkyl groups leads to the subject compounds with variations at $X_9$. When groups are present on the nucleus that are not stable to the catalytic hydrogenation conditions used to convert 6 to 7, we have found that reduction can be accomplished using sodium cyanoborohydride at slightly acidic pH. Further, formation of the N-alkyl quaternary salts of derivatives of 6 gives compounds that are also easily reduced with sodium borohydride, leading to derivatives of 7.

Space-filling representations of the low energy conformations for (+)-trans-10,11-dihydroxy-5,6,6a,7,8,12b-hexahydrobenzo[α]phenanthridine [(+)-dihydrexidine] and the 11bR enantiomer of dinoxyline that is homochiral to (+)-dihydrexidine at its 12bS chiral center have been compared. Two major structural features are readily evident. First, the steric bulk provided by the C(7)–C(8) ethano bridge in dihydrexidine (3) has been removed. Second, the angle of the pendent Scheme 1 Scheme for the synthesis of 8,9-dihydroxy-1,2,3,11b-tetrahydrochromeno[4,3,2-de]isoquinoline hydrobromide phenyl ring with respect to the plane of the catechol ring is changed slightly. This is most evident, in face-on views, where the aromatic hydrogen H(1) in dihydrexidine (3) projects above the catechol ring. In dinoxyline however, this position is used to tether the pendent phenyl ring through an oxygen atom, to the catechol ring; this forces the pendent phenyl ring to twist in a clockwise direction, relative to dihydrexidine (3), when viewed from above. The amino groups are in similar positions, given the degree of conformational flexibility of the heterocyclic rings. In addition, both molecules can present an N—H vector in an equatorial orientation, a feature of the pharmacophore believed to be important for $D_1$ receptor agonists. Consistent with those observations the pharmacological properties of these two molecules are similar.

Experiments have been conducted to determine the binding of dinoxyline at $D_1$ receptors. Dinoxyline was found to have similar affinity ($K_{0.5}$<5 nM) to dinapsoline for rat striatal $D_1$ receptors. In addition, competition experiments utilizing unlabeled SCH23390 (1) as a competitor demonstrated that dinoxyline competes with high affinity, having a shallow competition curve ($n_H$=ca. 0.7) consistent with agonist properties (see FIGS. 1 and 2). The agonist properties of dinoxyline at $D_1$ receptors were confirmed in vitro by measuring the ability of dinoxyline to increase cAMP production in rat striatum and C-6-m$D_1$ cells. In both rat striatum and C-6-mD, cells, dinoxyline has full agonist activity with an $EC_{50}$ of less than 30 nM in stimulating synthesis of cAMP via $D_1$ receptors.

Figure 2:
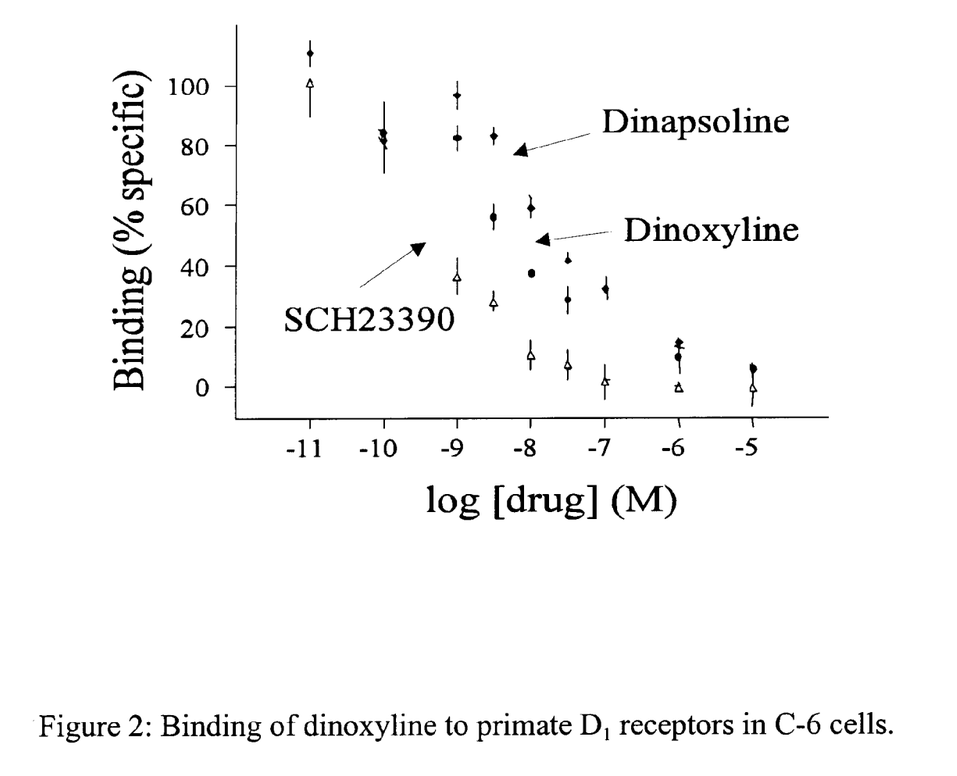
FIG. 2 is a graphic representation of the affinity of dinoxyline (circles), dinapsoline (diamonds) and (+)-SCH23390 (solid circles) for primate $D_1$ receptors expressed in C-6 cells. $D_1$ receptors were labeled with [$^3$H]SCH23390 (1), and unlabeled dinoxyline, dinapsoline, or (+)-SCH23390 was added to determine the specific binding of each compound to the $D_1$ receptor.
Figure 3:
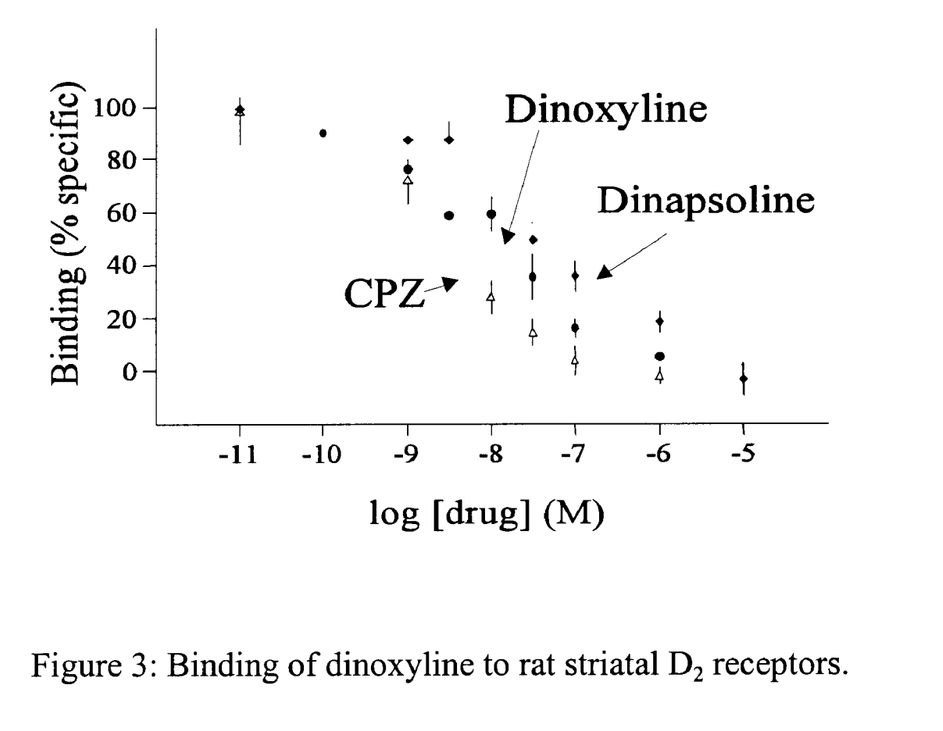
FIG. 3 is a graphic representation of the affinity of dinoxyline (circles), dinapsoline (diamonds), and chlorpromazine for striatal $D_2$ receptors labeled with [$^3$H]spiperone. Unlabeled dinoxyline, dinapsoline, or chlorpromazine was added to determine the specific binding of each compound to the $D_2$ receptor.

Thus, the pharmacological data confirm that dinoxyline has high affinity for dopamine $D_1$ receptors labeled with [$^3$H]SCH23390 that is slightly greater than that of (+)-trans-10,11-dihydroxy-5,6,6a,7,8,12b-hexahydrobenzo[α]phenan-thridine (dihydrexidine 3). Moreover, dinoxyline, in both rat striatal membranes and in cloned expressed primate $D_{1A}$ receptors, was a full agonist relative to dopamine, similar to dihydrexidine (3) but unlike the partial agonist (+)-SKF 38393 (see FIGS. 2 and 3: (+)-SKF 38393=(+)-2; (±)-trans-10,11-dihydroxy-5,6,6a,7,8,12b-hexa-hydrobenzo[α]phenanthridine=(±)-3, and (±)-8,9-dihydroxy-2,3,7,11b-tetrahydro-1H-naphtho[1,2,3-de]isoquinoline=4; dinapsoline).

Based on the underlying model of the $D_1$ pharmacophore, it is anticipated that both the affinity and intrinsic activity of racemic dinoxyline (and substituted analogs thereof) reside in only one of its enantiomers—the 11bR absolute configuration (and its homochiral analogs). Resolution of the racemate using art recognized separation techniques is expected to yield one dinoxyline isomer with approximately twice the $D_1$ affinity exhibited by the racemate.

Figure 1:
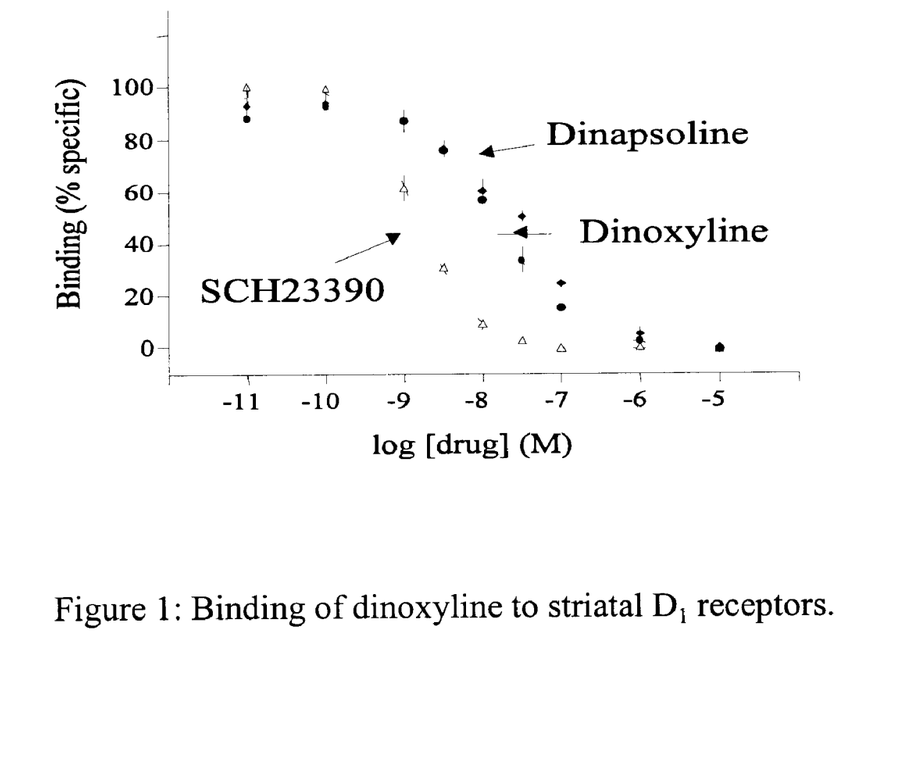
FIG. 1 is a graphic representation of the affinity of dinoxyline (circles), dinapsoline (diamonds) and (+)-SCH23390 (solid circles) for striatal $D_1$ receptors. Rat striatal $D_1$ receptors were labeled with [$^3$H]SCH23390 (1), and unlabeled dinoxyline, dinapsoline, or (+)-SCH23390 was added to determine the specific binding of each compound to the $D_1$ receptor.

Dihydrexidine was determined to be about ten-fold $D_1$:$D_2$ selective. In addition, dihydrexidine, while having the expected dopamine agonist activity, also had an unusual property termed herein as "functional selectivity". Specifically, in rats (in vivo or in vitro), dihydrexidine acts as an agonist at $D_2$-like receptors located post-synaptically, but as an antagonist at $D_2$-like receptors located pre-synaptically. Such is believed to be due to differences in the ligand-receptor-G protein complex located post-synaptically vs. pre-synaptically, as determined by the specific G proteins present in the given cellular milieu. As shown in FIG. 1, dinoxyline has greater affinity for $D_2$-like receptors than does dihydrexidine, providing the first full agonist having very high affinity for both $D_1$ and $D_2$ receptors in mammalian brain. Moreover, dinoxyline differs from dihydrexidine in its "functional selectivity" properties.

It has been shown that these $D_2$ properties of dihydrexidine reside in the same enantiomer (i.e., 6aR,12bS) that is the high affinity full agonist at the $D_1$ receptor. On this basis, it is expected that both the $D_1$ and $D_2$ properties of dinoxyline also reside in the homochiral enantiomer. The optical isomers of dinoxyline, and appropriate analogs, constitute significant tools to study the phenomena of "functional selectivity".

Figure 4:
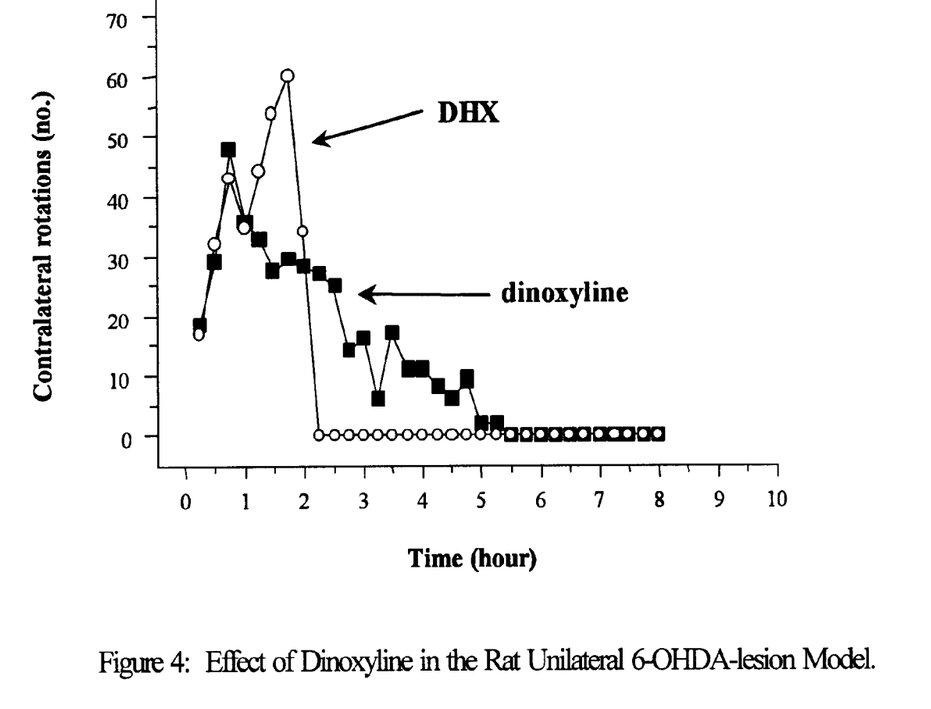
FIG. 4 is a graphic representation of the number of contralateral rotations over time (hours) in rats treated in the unilateral 6-OHDA lesion model with dinoxyline (squares) or dihydrexidine (circles).

The antiparkinsonian effects of dihydrexidine in the MPTP model of Parkinson's disease have been previously reported, and it is anticipated that dinoxyline will show similar effects. As shown in FIG. 4, dinoxyline has been tested in the rat unilateral 6-OHDA-lesion model, a paradigm that shows in vivo dopamine agonist activity, and has been proposed by some to predict antiparkinson drug efficacy. As can be seen, dinoxyline causes significant rotation that persists for approximately five hours after a single subcutaneous dose. This is more than twice the duration of action of a similar dose of dihydrexidine administered by the same route. Consistent with these data, preliminary studies have also been performed in marmosets having moderately-severe MPTP-induced dopamine denervation. Dinoxyline was found to have significant antiparkinson effects, causing an increase in locomotion and arousal, and a decrease in Parkinson signs. Accordingly dinoxyline and its derivatives have potential clinical utility in Parkinson's Disease and in other conditions where perturbation of dopamine receptors may be therapeutic. In addition, it has been reported that appropriate modification of dihydrexidine will produce analogs that can be targeted to specific subpopulations of the dopamine receptor family. Whereas similar strategies with dinoxyline should result in compounds with novel receptor subtype selectivity and/or functional profiles, the effect of these substitutions is not the same as with the dihydrexidine backbone.

Dopamine itself is seldom used as a drug because although it activates all dopamine receptors, it must be given intravenously, it has a very short pharmacokinetic half-life, and it also can activate other monoamine receptors. This series differs from earlier rigid dopamine analogs in several important ways. First, this is the first series of high affinity full $D_1$ agonists that also has at least equally high affinity for $D_2$ receptors. Thus, whereas dihydrexidine is ten-fold $D_1$:$D_2$ selective and dinapsoline is five-fold $D_1$:$D_2$ selective, dinoxyline actually has equally high affinity for both receptors. In the two earlier series, it was possible to increase the $D_2$ affinity, but only at the expense of $D_1$ affinity. This series provides the ability to have drugs with high affinity for both populations of receptors. Drugs with high affinity simultaneously for both the $D_1$ and $D_2$ offer specific clinical advantages over agents with high affinity for only one of the major families. The novelty of this series is clearer when the interaction with the specific dopamine receptor isoforms is examined. An important difference between this series and earlier drugs like dihydrexidine and dinapsoline is that those agents had essentially no affinity for the $D_4$ receptor isoform. Conversely, dinoxyline has a $K_{0.5}$ of less than 45 nM at the cloned human $D_4$ receptor, as compared to >1,000 for either dinapsoline or dihyrexidine or their derivatives. Although $D_4$ antagonists have been shown to lack efficacy in treating schizophrenia, there is great potential for the use of high efficacy $D_4$ agonists for selected psychiatric and neurological illnesses.

Another major difference with this series is the effect of substituents on receptor activity. It would have been predicted based on available data with dihydrexidine that N-propyl or N-allyl additions would markedly increase the $D_2$ affinity of the parent ligands. In fact, these N-substituents decreased the $D_2$ affinity of the parent compound significantly. This dramatic difference suggests that dinoxyline is binding to the $D_2$ receptor in an unexpected way, and should have unique therapeutic utility as well.

With reference to the following described experimental procedures, melting points were determined with a Thomas-Hoover melting point apparatus and are uncorrected. $^1$H NMR spectra were recorded with a Varian VXR 500S (500 MHZ) NMR instrument and chemical shifts were reported in values (ppm) relative to TMS. The IR spectra were recorded as KBr pellets or as a liquid film with a Perkin Elmer 1600 series FTIR spectrometer. Chemical ionization mass spectra (CIMS) were recorded on a Finnigan 4000 quadruple mass spectrometer. High resolution CI spectra were recorded using a Kratos MS50 spectrometer. Elemental analysis data were obtained from the microanalytical laboratory of Purdue University, West Lafayette, Ind.

THF was distilled from benzophenone-sodium under nitrogen immediately before use; 1,2-Dichloroethane was distilled from phosphorous pentoxide before use.

Example 1A

Synthesis of 8,9-Dihydroxy-1,2,3,11b-tetrahydrochromeno[4,3,2-de]isoquinoline Hydrobromide (Dinoxyline)

1,2-Dimethoxy-3-methoxymethoxybenzene (1).

A slurry of sodium hydride was prepared by adding 1000 ml of dry THF to 7.06 g (0.18 mol) of sodium hydride (60% dispersion in mineral oil) under an argon atmosphere at 0° C. To the slurry, 2,3-dimethoxy phenol (23.64 g; 0.153 mol) was added via syringe. The resulting solution was allowed to warm to room temperature and stirred for two hours. The black solution was cooled to 0° C. and 13.2 ml of chloromethyl methyl ether (14 g; 0.173 mol) was slowly added via syringe. The solution was allowed to reach room temperature and stirred for an additional 8 hours. The yellow mixture was concentrated to an oil that was dissolved in 1000 ml of diethyl ether. The resulting solution was washed with water (500 ml), 2N NaOH (3×400 ml), dried (MgSO$_4$), filtered, and concentrated. After Kugelrohr distillation (90–100° C., 0.3 atm), 24.6 g of a clear oil (84%) was obtained: $^1$H NMR: (300 MHz, CDCl$_3$): 6.97 (t, 1H, J=8.7 Hz); 6.79 (dd, 1H, J=7.2, 1.8 Hz); 6.62 (dd, 1H, J=6.9, 1.2 Hz); 5.21 (s, 2H); 3.87 (s, 3H); 3.85 (s, 3H); 3.51 (s, 3H). CIMS m/z: 199 (M+H$^+$, 50%); 167 (M+H$^+$—CH$_3$OH, 100%). Anal. Calc'd for C$_{10}$H$_{14}$O$_4$: C, 60.59; H, 7.12. Found: C, 60.93; H, 7.16.

2-(3,4-Dimethoxy-2-methoxymethoxyphenyl)-4,4,5,5-tetramethyl[1,3,2]dioxaborolane (2).

The MOM-protected phenol 1 (10 g; 0.0505 mol) was dissolved 1000 ml of dry diethyl ether and cooled to −78° C. A solution of n-butyl lithium (22.2 ml of 2.5 M) was then added via syringe. The cooling bath was removed and the solution was allowed to warm to room temperature. After stirring the solution at room temperature for two hours, a yellow precipitate was observed. The mixture was cooled to −78° C., and 15 ml of 2-isopropoxy-4,4,5,5-tetramethyl-1,3,2-dioxaborolane (0.080 mol) was added via syringe. The cooling bath was removed after two hours. Stirring was continued for four hours at room temperature. The mixture was then poured into 300 ml of water and extracted several times with diethyl ether (3×300 ml), dried ($Na_2SO_4$), and concentrated to a yellow oil (12.37 g, 76%) that was used without further purification: $^1H$ NMR: (300 MHz, $CDCl_3$): 7.46 (d, 1H, J=8.4 Hz); 6.69 (d, 1H, J=8.4 Hz); 5.15 (s, 2H); 3.87 (s, 3H); 3.83 (s, 3 H); 1.327 (s, 12H).

4-Bromo-5-nitroisoquinoline (3).

Potassium nitrate (5.34 g; 0.052 mol) was added to 20 ml of concentrated sulfuric acid and slowly dissolved by careful heating. The resulting solution was added dropwise to a solution of 4-bromoisoquinoline (10 g; 0.048 mol) dissolved in 40 ml of the same acid at 0° C. After removal of the cooling bath, the solution was stirred for one hour at room temperature. The reaction mixture was then poured onto crushed ice (400 g) and made basic with ammonium hydroxide. The resulting yellow precipitate was collected by filtration and the filtrate was extracted with diethyl ether (3×500 ml), dried ($Na_2SO_4$), and concentrated to give a yellow solid that was combined with the initial precipitate. Recrystallization from methanol gave 12.1 g (89%) of slightly yellow crystals: mp 172–174° C.; $^1H$ NMR: (300 MHz, $CDCl_3$): 9.27 (s, 1H); 8.87 (s, 1H); 8.21 (dd, 1H, J=6.6, 1.2 Hz); 7.96 (dd, 1 H, J=6.6, 1.2 Hz); 7.73 (t, 1 H, J=7.5 Hz). CIMS m/z: 253 (M+H$^+$, 100%); 255 (M+H$^+$+2, 100%). Anal. Calc'd for $C_9H_5BrN_2O_2$: C, 42.72; H, 1.99; N, 11.07. Found: C, 42.59; H, 1.76; N, 10.87.

4-(3,4-Dimethoxy-2-methoxymethoxyphenyl)-5-nitroisoquinoline (4).

Isoquinoline 3 (3.36 g; 0.0143 mol), pinacol boronate ester 2 (5.562 g; 0.0172 mol), and 1.0 g (6 mol %) of tetrakis(triphenylphosphine)palladium(0) were suspended in 100 ml of dimethoxyethane (DME). Potassium hydroxide (3.6 g; 0.064 mol), and 0.46 g (10 mol %) of tetrabutylammonium bromide were dissolved in 14.5 ml of water and added to the DME mixture. The resulting suspension was degassed for 30 minutes with argon and then heated at reflux for four hours. The resulting black solution was allowed to cool to room temperature, poured into 500 ml of water, extracted with diethyl ether (3×500 ml), dried ($Na_2SO_4$), and concentrated. The product was then purified by column chromatography (silica gel, 50% ethyl acetate: hexane) giving 5.29 g of yellow crystals (80.1%): mp 138–140° C.; $^1H$ NMR: (300 MHz, $CDCl_3$): 9.33 (s, 1H); 8.61 (s, 1H); 8.24 (dd, 1H, J=7.2, 0.9 Hz); 8.0 (dd, 1H, J=6.3, 1.2 Hz); 7.67 (t, 1H, J=7.8 Hz); 7.03 (d, 1H, J=9.6 Hz); 6.81 (d, 1H, J=8.1 Hz); 4.86 (d, 1H, J=6 Hz); 4.70 (d, 1H, J=5.4 Hz); 3.92 (s, 3H); 3.89 (s, 3 H); 2.613 (s, 3 H). CIMS mlz: 371 (M+H$^+$, 100%). Anal Calc'd for $C_{19}H_{18}N_2O_6$: C, 61.62; H, 4.90; N, 7.56. Found: C, 61.66; H, 4.90; N, 7.56.

2,3-Dimethoxy-6-(5-nitroisoquinolin-4-yl)phenol (5).

After dissolving isoquinoline 4 (5.285 g, 0.014 mol) in 200 ml of methanol by gentle heating, p-toluenesulfonic acid monohydrate (8.15 g; 0.043 mol) was added in several portions. Stirring was continued for four hours at room temperature. After completion of the reaction, the solution was made basic by adding saturated sodium bicarbonate. The product was then extracted with dichlormethane (3×250 ml), dried ($Na_2SO_4$), and concentrated. The resulting yellow solid (4.65 g; 98%) was used directly in the next reaction. An analytical sample was recrystallized from methanol: mp 170–174° C.; $^1H$ NMR: (300 MHz, $CDCl_3$): 9.33 (s, 1H); 8.62 (s, 1H); 8.24 (dd, 1H, J=7.2, 0.9 Hz); 7.99 (dd, 1H, J=6.3, 1.2 Hz); 7.67 (t, 1H, J=7.8 Hz); 6.96 (d, 1H, J=8.7 Hz); 6.59 (d, 1H, J=8.7 Hz); 5.88 (bs, 1H); 3.94 (s, 3H); 3.92 (s, 3H). CIMS mn/z: 327 (M+H$^+$, 100%). Anal Calc'd for $C_{17}H_{14}N_2O_5$: C, 62.57; H, 4.32; N, 8.58; Found: C, 62.18; H, 4.38; N, 8.35.

8,9-dimethoxychromeno[4,3,2-de]isoquinoline (6).

Phenol 5 (4.65 g, 0.014 mol) was dissolved in 100 ml of dry N,N-dimethylformamide. The solution was degassed with argon for thirty minutes. Potassium carbonate (5.80 g, 0.042 mol) was added to the yellow solution in one portion. After heating at 80° C. for one hour, the mixture had turned brown and no more starting material remained. After the solution was cooled to room temperature, 200 ml of water was added. The aqueous layer was extracted with dichloromethane (3×500 ml), this organic extract was washed with water (3×500 ml), dried ($Na_2SO_4$), and concentrated. A white powder (3.65 g 92%) was obtained that was used in the next reaction without further purification. An analytical sample was recrystallized from ethyl acetate:hexane: mp 195–196° C.; $^1H$ NMR: (300 MHz, $CDCl_3$): 9.02 (s, 1H); 8.82 (s, 1H); 7.87 (d, 1H, J=8.7 Hz); 7.62 (m, 3H); 7.32 (dd, 1H, J=6.0, 1.5 Hz); 6.95 (d, J=9.6 Hz); 3.88 (s, 3H); 3.82 (s, 3H). CIMS m/z: 280 (M+H$^+$, 100%).

8,9-dimethoxy-1,2,3,11b-tetrahydrochromeno[4,3,2-de]isoquinoline (7).

Platinum (IV) oxide (200 mg) was added to a solution containing 50 ml of acetic acid and isoquinoline 6 (1 g; 3.5 mmol). After adding 2.8 ml of concentrated HCl, the mixture was shaken on a Parr hydrogenator at 60 psi for 24 hours. The green solution was filtered through Celite to remove the catalyst and the majority of the acetic acid was removed by rotary evaporation. The remaining acid was neutralized using a saturated sodium bicarbonate solution, extracted with diethyl ether (3×250 ml), dried ($Na_2SO_4$), and concentrated. The resulting oil (0.997 g; 99%) was used without further purification: $^1H$ NMR: (300 MHz, $CDCl_3$): 7.10 (t, 1H, J=7.5 Hz); 7.00 (d, 1H, J=8.4 Hz); 6.78 (m, 2H); 6.60 (d, 1H, J=9 Hz); 4.10 (s, 2H); 3.84 (m, 8H); 2.93 (t, 1H, J=12.9 Hz).

8,9-dihydroxy-1,2,3,11b-tetrahydrochromeno[4,3,2-de]isoquinoline Hydrobromide (8).

The crude 7 (0.834 g; 3.0 mmol) was dissolved in 50 ml of anhydrous dichloromethane. The solution was cooled to −78° C. and 15.0 ml of a boron tribromide solution (1.0 M in dichloromethane) was slowly added. The solution was stirred overnight, while the reaction slowly warmed to room temperature. The solution was recooled to −78° C., and 50 ml of methanol was slowly added to quench the reaction. The solution was then concentrated to dryness. Methanol was added and the solution was concentrated. This process was repeated three times. The resulting brown solid was treated with activated charcoal and recrystallized from ethanol: mp 298–302° C. dec; $^1H$ NMR: (300 MHz, $D_2O$): 7.32 (t, 1H, J=6.6 Hz); 7.13 (d, 1H, J=8.4 Hz); 7.04 (d, 1H, J=8.4 Hz); 4.37 (m, 2H); 4.20 (t, 3H, J=10 Hz.). Anal. Calc'd for $C_{15}H_{14}BrNO_3 \cdot H_2O$: C, 50.87; H, 4.55; N, 3.82. Found: C, 51.18; H, 4.31; N, 3.95.

N-Allyl-8,9-dimethoxy-1,2,3,11b-tetrahydrochromeno[4,3,2-de]isoquinoline (10).

Tetrahydroisoquinoline 7(1.273 g; 4.5 mmol) was dissolved in 150 ml of acetone. Potassium carbonate (0.613 g; 4.5 mmol) and 0.4 ml (4.6 mmol) of allyl bromide were added. The reaction was stirred at room temperature for four hours. The solid was then removed by filtration and washed on the filter several times with ether. The filtrate was concentrated and purified by flash chromatography (silica gel, 50% ethyl acetate:hexane) to give 1.033 g (71%) of a yellow oil that was used without further purification: $^1$H NMR: (300 MHz, CDCl$_3$): 7.15 (t, 1H, J=9 Hz); 7.04 (d, 1H, J=9 Hz); 6.83 (m, 2H); 6.65 (d, 1H, J=6 Hz); 5.98 (m, 1H); 5.27 (m, 2H); 4.10 (m, 3H); 3.95 (s, 3H); 3.86 (s, 3H); 3.46 (d, 1H, J=15 Hz); 3.30 (d, 2H, J=6 Hz); 2.56 (t, 1H, J=12 Hz).

N-Allyl-8,9-dihydroxy-1,2,3,11b-tetrahydrochromeno[4,3,2-de]isoquinoline (11).

N-Allyl amine 10 (0.625 g; 1.93 mmol) was dissolved in 50 ml of dichloromethane. The solution was cooled to −78° C. and 10.0 ml of BBr$_3$ solution (1.0 M in dichloromethane) was slowly added. The solution was stirred overnight, while the reaction slowly warmed to room temperature. After recooling the solution to 78° C., 50 ml of methanol was slowly added to quench the reaction. The reaction was then concentrated to dryness. Methanol was added and the solution was concentrated. This process was repeated three times. Recycstallization of the brown solid from ethanol gave 0.68 g (61%) of a white solid: mp 251–253° C. dec; $^1$H NMR: (300 MHz, D$_2$O): 10.55 (s, 1H); 10.16 (s, 1H); 8.61 (t, 1H, J=9 Hz); 8.42 (d, 1H, J=9 Hz); 8.31 (d, 1H, J=9 Hz); 7.87 (d, 1H, J=9 Hz); 7.82 (d, H, J=9 Hz); 7.36 (q, 1H, J=9 Hz); 6.89 (m, 2H); 6.85 (d, 1H, J=15 Hz); 5.58 (m, 3H); 5.28 (m, 2H); 3.76 (d, 1H, J=3 Hz). HRCIMS m/z: Calc'd: 295.1208; Found: 295.1214.

N-Propyl-8,9-dimetboxy-1,2,3,11b-tetrahydrochromeno-(4,3,2-de)-isoquinoline (12).

N-Allyl amine 10 (1.033 g; 3.2 mmol) was dissolved in 50 ml of ethanol. Palladium on charcoal (10% dry; 0.103 g) was then added. The mixture was shaken on a Parr hydrogenator under 60 psi H$_2$ for 3 hours. After TLC showed no more starting material, the mixture was filtered through Celite and concentrated to give 0.95 g (91%) of an oil that was used without further purification: $^1$H NMR: (300 MHz, CDCl$_3$): 7.15 (t, 1H, J=7.2 Hz); 7.04 (d, 1H, J=8.1 Hz); 6.84 (t, 2H, J=Hz); 6.65 (d, 1H, J=8.4 Hz); 4.07 (m, 2H); 3.95 (s, 3H); 3.86 (s, 3H); 3.71 (q, =5.1 Hz); 3.42 (d, 2H,J=15.6 Hz); 2.62 (m, 2H); 2.471 (t, J=10.5 Hz); 1.69 (h, J=7.2 Hz); 0.98 (t, 3H, J=7.5 Hz). CIMS m/z: 326 (M+H+, 100%).

N-Propyl-8,9-dihydroxy-1,2,3,11b-tetrahydrochromeno [4,3,2-de]isoquinoline (13).

The N-propyl amine 12 (0.90 g; 2.8 mmol) was dissolved in 200 ml of dichloromethane and cooled to −78° C. In a separate 250 ml round bottom flask, 125 ml of dry dichloromethane was cooled to −78° C., and 1.4 ml (14.8 mmol) of BBr$_3$ was added via syringe. The BBr$_3$ solution was transferred using a cannula to the flask containing the starting material. The solution was stirred overnight, while the reaction slowly warmed to room temperature. After recooling the solution to −78° C., 50 ml of methanol was slowly added to quench the reaction. The reaction was then concentrated to dryness. Methanol was added and the solution was concentrated. This process was repeated three times. The resulting tan solid was suspended in hot isopropyl alcohol. Slowly cooling to room temperature resulted in a fine yellow precipitate. The solid was collected by filtration (0.660 g; 63%): mp 259–264° C. dec; $^1$H NMR: (300 MHz, CDCl$_3$): 7.16 (t, 1H, J=9 Hz); 6.97 (d, 1H, J=12 Hz); 6.83 (d, 1H, J=9 Hz); 6.55 (d, 1H, J=9 Hz); 6.46 (d, 1H, J=9 Hz); 4.45 (d, 1H, J=15 Hz); 4.10 (m, 3H); 3.17 (q, 2H, J=6 Hz); 3.04 (t, 1H, J=9 Hz); 1.73 (q, 2H, J=9 Hz); 0.90 (t, 3H, J=6 Hz). Anal. Calc'd. for $C_{18}H_{20}BrNO_3$: C, 57.16; H, 5.33; N, 3.70. Found: C, 56.78; H, 5.26; N, 3.65.

Pharmacology of Dinoxyline
Methods: Radioreceptor Studies in Brain Tissue

Frozen rat striata was homogenized by seven manual strokes in a Wheaton Teflon-glass homogenizer in 8 ml ice cold 50 mM HEPES buffer with 4.0 mM MgCl$_2$, (pH 7.4). The tissue was centrifuged at 27,000×g for 10 min, the supernatant was discarded, and the pellet was homogenized (5 strokes) and resuspended in ice cold buffer and centrifuged again. The final pellet was suspended at a concentration of approximately 2.0 mg wet weight/ml. The amount of tissue added to each assay tube was 1.0 mg, in a final assay volume of 1.0 ml. D$_1$ receptors were labeled with [$^3$H] SCH23390 (0.30 nM). D$_2$ receptors were labeled with [$^3$H] spiperone (0.07 nM); unlabeled ketanserin (50 nM) was added to mask binding to 5HT$_2$ sites. Total binding was defined as radioligand bound in the absence of any competing drug. Nonspecific binding was estimated by adding unlabeled SCH23390 (1 $\mu$M) or unlabeled chlorpromazine (1 M) for D$_1$ and D$_2$ receptor binding assays, respectively. Triplicate determinations were made for each drug concentration in each assay. Assay tubes were incubated at 37° C. for 15 minutes. Binding was terminated by filtering with ice cold buffer on a Skatron 12 well cell harvester (Skatron, Inc., Sterling, Va.) using glass fiber filter mats (Skatron no. 7034). Filters were allowed to dry and 2.0 ml of Optiphase HI-SAF II scintillation fluid was added. After shaking for 30 minutes, radioactivity was determined on a LKB Wallac 1219 Rack-Beta liquid scintillation counter (Wallac, Gaithersburg, Md.). Tissue protein levels were estimated using the BCA protein assay reagent.

Functional Studies in Brain Tissue

Frozen striatal tissue (ca. 40 mg) was homogenized in 4 ml of buffer (5 n-mM Hepes, 2 mM EGTA, pH 7.5) using 10 strokes in a Wheaton Teflon-glass homogenizer. Four ml of 50 mM Hepes with 2 mM EGTA buffer (pH 7.5) was added, and the tissue was homogenized by an additional 3 strokes. A 20 $\mu$l aliquot of this tissue homogenate was added to a prepared reaction. The reaction mixture consisted of 100 mM Hepes (pH 7.4), 100 mM NaCl, 4 mM MgCl$_2$, 2 mM EDTA, 500 $\mu$M isobutyl methylxanthine (IBMX), 0.01% ascorbic acid, 10 $\mu$M pargyline, 2 mM ATP, 5 $\mu$M GTP, 20 mM phosphocreatine, 5 units of creatine phosphokinase (CPK), and selected concentrations of DA. The final reaction volume was 100 $\mu$l. Basal cAMP activity was determined by incubation of tissue in the reaction mixture with no drug added. Tubes were assayed in duplicate. After a 15 min incubation at 30° C., the reaction was stopped with the addition of 500 $\mu$l of 0.1 N HCl. Tubes were vortexed briefly, and then spun in a BHG Hermle Z 230 M microcentrifuge for five min at 15,000×g to eliminate large particles.

The concentration of cAMP in each sample was determined with an RIA of acetylated cAMP, modified from that previously described (Harper and Brooker, 1975). Iodination of cAMP was performed using a method described previously (Patel and Linden, 1988). Assay buffer was 50 mM sodium acetate buffer with 0.1% sodium azide (pH 4.75). Standard curves of cAMP were prepared in buffer at concentrations of 2 to 500 fmoles/assay tube. To improve assay sensitivity, all samples and standards were acetylated with 10 $\mu$l of a 2:1 solution of triethylamine:acetic anhydride. Samples were assayed in duplicate. Each assay tube contained 100 $\mu$l of diluted sample, 100 $\mu$l of primary antibody (sheep, anti-cAMP, 1:100,000 dilution with 1% BSA in buffer) and 100 $\mu$l of [$^{125}$I]-cAMP (50,000 dpm/100 $\mu$l of buffer); total assay volume was 300 $\mu$l. Tubes were vortexed and stored at 4° C. overnight (approx. 18 hr). Antibody-bound radioactivity was then separated by the addition of 25

μL of BioMag rabbit, anti-goat IgG (Advanced Magnetics, Cambridge Mass.), followed by vortexing and further incubation at 4° C. for 1 hr. To these samples 1 ml of 12% polyethylene glycol/50 mM sodium acetate buffer (pH 6.75) was added and all tubes were centrifuged at 1700×g for 10 min. Supernatants were aspirated and radioactivity in the resulting pellet was determined using an LKB Wallac gamma counter (Gaithersburg, Md.).

Radioreceptor Studies with Expressed Receptors

Radioreceptor and function studies were also conducted for cloned human or monkey receptors transfected into one of several cell lines [e.g., C-6 glioma or Chinese hamster ovary (CHO) cells]. Cells were grown in appropriate medium, and at confluency, harvested for membrane preparation. Flasks of cells in the same passage were scraped using a rubber policeman and collected in 50 ml centrifuge tubes. These were spun for 10 min at 1200×g, to pellet whole cells. The supernatant was discarded and then five ml of PBS (phosphate buffered saline)/flask was added to the centrifuge tubes to resuspend the cells. The tubes were then centrifuged again for 20 min at 28,500×g. The PBS was removed and the pellet suspended in a solution of 10% DMSO in PBS. Cells were homogenized with a polytron for 10 seconds on setting 5. One ml aliquots were stored at −80° C. until use in receptor binding studies. Aliquots contained approximately 1 mg/ml of protein, as measured using the BCA protein assay reagent (Pierce, Rockford, Ill.).

For $D_1$-like receptors, membrane protein (50–75 g was incubated with each test compound and [$^3$H] SCH23390 (0.3 nM) in 50 mM Tris-HCl (pH 7.4), with 120 mM NaCl, 5 mM KCl, 2 mM $CaCl_2$ and 1 mM $MgCl_2$. SCH23390 (5 μM) was used to define nonspecific binding. Tubes were run in triplicate in a final volume of 500 μl. After incubation for 30 minutes at 37° C., tubes were filtered rapidly through Skatron glass fiber filter mats (11734), and rinsed with 5 ml of ice-cold wash buffer (50 mM Tris, pH 7.4) using a Skatron Micro Cell Harvester (Skatron Instruments Inc., Sterling, Va.). Filters were allowed to dry, then punched into scintillation vials (Skatron Instruments Inc., Sterling, Va.). OptiPhase 'HiSafe' II scintillation cocktail (1 ml) was added to each vial. After shaking for 30 min, radioactivity in each sample was determined on an LKB Wallac 1219 Rackbeta liquid scintillation counter (Wallac Inc., Gaithersburg, Md.). A similar protocol was used for $D_2$-like receptors, except that [$^3$H] spiperone (0.07 nM) was used as the radioligand.

Functional Studies with Expressed Receptors

Agonist intrinsic activity was assessed by the ability of selected compounds to stimulate adenylate cyclase, as measured by cAMP formation in whole cells. In C-6 cells, for example, the dose response curve for each drug was fit using a sigmoid function to determine maximal effective concentration (top plateau of curve) as well as $EC_{50}$s. All drugs were run in the same assay in order to decrease variability across cell passages. Confluent plates of cells were incubated with drugs dissolved in DMEM-H plain media supplemented with 20 mM Hepes, 0.01% ascorbic acid and 500 μM iso-butyl-methyl xanthine (IBMX; pH 7.2; media A). The final volume for each well was 500 μl. In addition to the dose response curves run for each drug, basal levels of cAMP and isoproterenol-stimulated (through endogenous $\beta_2$ receptors, positive control) cAMP levels were evaluated for each plate. Each condition was run in duplicate wells. Following a 10 min incubation at 37° C., cells were rinsed briefly with media, and the reaction stopped with the addition of 500 μl 0.1 N HCl. Cells were then allowed to chill for 5–10 min at 4° C., the wells were scraped and the volume placed into 1.7 ml centrifuge tubes. An additional 1 ml of 0.1 N HCl was added to each tube, for a final volume of 1.5 ml/tube. Tubes were vortexed briefly, and then spun in a BHG Hermle Z 230 M microcentrifuge for five min at 15,000×g to eliminate large cellular particles. Cyclic AMP levels for each sample were determined as described above.

Data were calculated for each sample, and expressed initially as pmol/mg/min cAMP. Baseline values of cAMP were subtracted from the total amount of cAMP produced for each drug condition. To minimize interassay variation, a reference compound (DA; 100 μM) was included in each assay to serve as an internal standard that allowed normalization of the data. Data for each drug were expressed relative to the percentage of the stimulation produced by 100 M DA. Normalized dose-response curves were analyzed by nonlinear regression using an algorithm for sigmoid curves in the curvefitting program InPlot (Graphpad, Inc.; San Francisco, Calif.). For each curve, the program provided point estimates of both the $EC_{50}$ and the maximal stimulation produced (i.e., top plateau of sigmoid curve).

Additional Claimed Variations of the Subject Compounds

Using the same general procedures described in Example 1 above, the compounds of Examples 1–56 as set forth in Table II below are synthesized using starting compounds corresponding to those illustrated in Scheme 1, but substituted with functional groups appropriate to provide the substitution patterns depicted on the fused chromenoisoquinoline product shown for each Example. Thus, for example, 6, 7 and/or 8 substituted analogs of compound 3 (scheme 1) provide the corresponding substituents $R_6$, $R_5$, and $R_4$, respectively, on Formula I. Use of other 1 and 3 substituted isoquinolines (analogs of compound 3 in scheme 1) provided corresponding substitution patterns at $C_3$ and $C_1$ in Formula I.

| Example Number | $R_1$ | $R_2$ | $R_3$ | $R_4$ | $R_5$ | $R_6$ | $R_8$ | $X_9$ |
|---|---|---|---|---|---|---|---|---|
| 1B | H | H | H | $CH_3$ | H | H | H | OH |
| 2 | H | H | H | H | $CH_3$ | H | H | OH |
| 3 | H | H | H | H | H | $CH_3$ | H | OH |
| 4 | H | H | H | $C_6H_5$ | H | H | H | OH |
| 5 | $CH_3$ | H | $CH_3$ | $CH_3$ | H | H | H | OH |
| 6 | H | H | $C_3H_7$ | H | $CH_3$ | H | H | OH |
| 7 | H | H | H | $C_2H_5$ | H | H | H | OH |
| 8 | H | H | H | H | $C_2H_5$ | H | H | OH |
| 9 | H | H | H | H | $CH_3$ | $CH_3$ | H | Cl |
| 10 | $CH_3$ | H | $C_3H_7$ | $CH_3$ | $CH_3$ | H | H | OH |
| 11 | $CH_3$ | H | $C_2H_5$ | H | $CH_3$ | $CH_3$ | H | Cl |
| 12 | $CH_3$ | H | $CH_3$ | H | H | $C_2H_5$ | H | OH |

-continued

| Example Number | $R_1$ | $R_2$ | $R_3$ | $R_4$ | $R_5$ | $R_6$ | $R_8$ | $X_9$ |
|---|---|---|---|---|---|---|---|---|
| 13 | $CH_3$ | H | $C_4H_9$ | H | OH | H | H | OH |
| 14 | H | H | H | $CH_3$ | OH | H | H | OH |
| 15 | H | H | H | H | F | H | H | OH |
| 16 | H | H | H | OH | H | H | H | Cl |
| 17 | H | H | H | Br | H | H | H | OH |
| 18 | H | $CH_3$ | H | H | Br | H | H | $OCH_3$ |
| 19 | H | $CH_3$ | H | H | H | Br | H | $OCH_3$ |
| 20 | H | $CH_3$ | H | $CH_3$ | Br | H | H | $OCH_3$ |
| 21 | $CH_3$ | H | $CH_3$ | F | H | H | H | OH |
| 22 | $CH_3$ | H | $CH_3$ | H | F | H | H | OH |
| 23 | $CH_3$ | H | $CH_3$ | H | H | F | H | OH |
| 24 | $C_2H_5$ | H | $C_2H_5$ | H | OH | H | H | F |
| 25 | $C_2H_5$ | H | $C_2H_5$ | $CH_3$ | OH | H | H | F |
| 26 | $C_2H_5$ | H | $C_2H_5$ | $CH_3O$ | H | $CH_3$ | H | F |
| 27 | $C_3H_7$ | H | $C_3H_7$ | H | $CH_3O$ | H | H | Cl |
| 28 | $C_3H_7$ | H | $C_3H_7$ | H | $CH_3$ | $CH_3O$ | H | Cl |
| 29 | $C_3H_7$ | H | $C_3H_7$ | $C_2H_5O$ | H | H | H | OH |
| 30 | $C_3H_7$ | H | $C_3H_7$ | H | H | OH | H | OH |
| 31 | $C_4H_9$ | H | $C_4H_9$ | $CH_3$ | H | H | H | OH |
| 32 | $C_4H_9$ | H | $C_4H_9$ | H | OH | $CH_3$ | H | OH |
| 33 | $C_4H_9$ | H | $C_4H_9$ | OH | Cl | H | H | OH |
| 34 | $C_4H_9$ | H | $C_4H_9$ | OH | Cl | H | H | OH |
| 35 | H | H | H | H | H | H | H | H |
| 36 | H | H | H | $CH_3$ | H | H | H | H |
| 37 | H | H | H | H | $CH_3$ | H | H | H |
| 38 | H | H | H | H | H | $CH_3$ | H | H |
| 39 | H | H | H | H | H | H | $CH_3$ | OH |
| 40 | H | H | H | H | H | H | $CH_2(CH_3)_2$ | OH |
| 41 | H | H | H | H | H | H | $CH_3$ | H |
| 42 | H | H | H | H | H | H | $CH_2(CH_3)_2$ | H |
| 43 | H | H | H | $CH_3$ | H | H | $CH_3$ | OH |
| 44 | H | H | H | H | $CH_3$ | H | $CH_3$ | OH |
| 45 | H | H | H | H | H | $CH_3$ | $CH_3$ | OH |
| 46 | H | H | H | H | H | H | $CH_2CH_3$ | OH |
| 47 | H | $C_3H_5$ | H | H | $CH_3$ | H | H | OH |
| 48 | H | $C_3H_5$ | H | H | H | H | OH | H |
| 49 | H | $C_3H_5$ | H | H | H | H | H | $OCH_3$ |
| 50 | H | $C_3H_5$ | H | H | $C_2H_5$ | H | H | OH |
| 51 | H | $C_3H_5$ | H | $CH_3$ | H | $OCH_3$ | H | OH |
| 52 | H | $C_3H_5$ | H | H | H | H | H | $OCH_3$ |
| 53 | H | $C_3H_5$ | H | H | $CH_3$ | H | H | $OCH_3$ |
| 54 | H | $C_3H_5$ | H | H | H | H | H | OH |
| 55 | H | $C_3H_5$ | H | H | $C_2H_5$ | H | H | OH |
| 56 | H | $C_3H_5$ | H | $OCH_3$ | H | $C_2H_5$ | H | OH |

The foregoing examples are illustrative of the invention and are not intended to limit the invention to the disclosed compounds. Variations and modifications of the exemplified compounds obvious to one skilled in the art are intended to be within the scope and nature of the invention as specified in the following claims.

What is claimed is:

1. A compound of the formula and pharmaceutically acceptable salts thereof wherein $R_1$, $R_2$, and $R_3$ are hydrogen, $C_1$–$C_4$ alkyl, or $C_2$–$C_4$ alkenyl;

$R_8$ is hydrogen, $C_1$–$C_4$ alkyl or a phenoxy protecting group;

$X_9$ is hydrogen, halo or a group of the formula —OR wherein R is hydrogen, $C_1$–$C_4$ alkyl or a phenoxy protecting group, and further when $X_9$ is a group of the formula —OR, the groups $R_8$ and R can be taken together to form a group of the formula —$CH_2$—; and $R_4$, $R_5$, and $R_6$ are independently selected from the group consisting of hydrogen, $C_1$–$C_4$ alkyl, phenyl, halo, or a group —OR wherein R is as defined above.

2. The compound of claim 1 wherein $X_9$ is hydroxy and $R_8$ is hydrogen.

3. The compound of claim 1 wherein $R_1$, $R_2$, and $R_3$ are hydrogen.

4. The compound of claim 2 wherein $R_1$, $R_2$ and $R_3$ are hydrogen.

5. The compound of claim 1 wherein $R_1$, $R_3$, $R_4$, $R_5$ and $R_6$ are each hydrogen.

6. The compound of claim 1 wherein $X_9$ and $R_8$ are hydrogen.

7. The compound of claim 1 wherein $R_1$ and $R_3$ are hydrogen.

8. The compound of claim 1 wherein $R_1$ and $R_3$ are $C_1$–$C_4$ alkyl.

9. The compound of claim 1 wherein $R_2$ is $C_2$–$C_4$ alkenyl.

10. A method for treating a patient suffering from Parkinson's disease, said method comprising the step of administering to the patient in need of said treatment an effective amount of a compound of the formula:

wherein
- $R_1$, $R_2$ and $R_3$ are hydrogen, $C_1$–$C_4$ alkyl or $C_2$–$C_4$ alkenyl;
- $R_8$ is hydrogen, $C_{114}$ $_{C4}$ alkyl or a phenoxy protecting group;
- $X_9$ is hydrogen, halo or a group of the formula —OR wherein R is hydrogen, $C_1$–$C_4$ alkyl or a phenoxy protecting group, and further when $X_9$ is a group of the formula —OR, the groups R and $R_8$ can be taken together to form a group of the formula —$CH_2$—;
- $R_4$, $R_5$ and $R_6$ are independently selected from the group consisting of hydrogen, $C_1$–$C_4$ alkyl, phenyl, halo, or a group —OR wherein R is as defined above;

or a pharmaceutically acceptable salt thereof in an amount effective to reduce the symptoms of said disorder.

11. The method of claim 10 wherein $X_9$ is hydroxy and $R_8$ is hydrogen.

12. The method of claim 10 wherein $R_1$, $R_2$, and $R_3$ are hydrogen.

13. The method of claim 11 wherein $R_1$, $R_2$ and $R_3$ are hydrogen.

14. The method of claim 10 wherein $R_1$, $R_3$, $R_4$, $R_5$ and $R_6$ are each hydrogen.

15. The method of claim 10 wherein $X_9$ and $R_8$ are hydrogen.

16. The method of claim 10 wherein $R_1$ and $R_3$ are hydrogen.

17. The method of claim 10 wherein $R_1$ and $R_3$ are $C_1$–$C_4$ alkyl.

18. The method of claim 10 wherein $R_2$ is $C_2$–$C_4$ alkenyl.

19. A pharmaceutical composition comprising a therapeutically effective amount of a compound of the formula:

or a pharmaceutically acceptable salt thereof wherein
- $R_1$, $R_2$ and $R_3$ are hydrogen or $C_1$–$C_4$ alkyl;
- $R_8$ is hydrogen, $C_1$–$C_4$ alkyl or a phenoxy protecting group;
- $X_9$ is hydrogen, halo or a group of the formula —OR wherein R is hydrogen, $C_1$–$C_4$ alkyl or a phenoxy protecting group, and further when $X_9$ is a group of the formula —OR, the groups R and $R_8$ can be taken together to form a group of the formula —$CH_2$—;
- $R_4$, $R_5$ and $R_6$ are independently selected from the group consisting of hydrogen, $C_1$–$C_4$ alkyl, phenyl, halo, or a group —OR wherein R is as defined above;

and a pharmaceutically acceptable carrier therefor.

20. The composition of claim 19 wherein $X_9$ is hydroxy and $R_8$ is hydrogen.

21. The composition of claim 19 wherein $R_1$, $R_2$, and $R_3$ are hydrogen.

22. The composition of claim 20 wherein $R_1$, $R_2$ and $R_3$ are hydrogen.

23. The composition of claim 20 wherein $R_2$ is $C_1$–$C_4$ alkyl.

24. The composition of claim 19 wherein $R_2$ is $C_2$–$C_4$ alkenyl.

25. The composition of claim 19 wherein at least one of $R_4$, $R_5$ or $R_6$ is hydrogen.

26. The composition of claim 19 wherein at least two of $R_4$, $R_5$ or $R_6$ is hydrogen.

* * * * *

UNITED STATES PATENT AND TRADEMARK OFFICE
CERTIFICATE OF CORRECTION

PATENT NO. : 6,413,977 B1
DATED : July 2, 2002
INVENTOR(S) : Nichols et al.

It is certified that error appears in the above-identified patent and that said Letters Patent is hereby corrected as shown below:

Column 19,
Lines 2-33, should read
-- 10. A method for treating a patient suffering from Parkinson's disease, said method comprising the step of administering to the patient in need of said treatment an effective amount of a compound of the formula:

wherein
$R_1$, $R_2$ and $R_3$ are hydrogen, $C_1$-$C_4$ alkyl or $C_2$-$C_4$ alkenyl;
$R_8$ is hydrogen $C_1$-$C_4$ alkyl or a phenoxy protecting group;
$X_9$ is hydrogen, halo or a group of the formula -OR wherein R is hydrogen, $C_1$-$C_4$ alkyl or a phenoxy protecting group, and further when $X_9$ is a group of the formula -OR, the groups R and $R_8$ can be taken together to form a group of the formula -$CH_2$-;
$R_4$, $R_5$ and $R_6$ are independently selected from the group consisting of hydrogen, $C_1$-$C_4$ alkyl, phenyl, halo, or a group -OR wherein R is as defined above;
or a pharmaceutically acceptable salt thereof in an amount effective to reduce the symptoms of said disorder. --

Signed and Sealed this

Twenty-fourth Day of December, 2002

JAMES E. ROGAN
*Director of the United States Patent and Trademark Office*